United States Patent
Grusin et al.

(10) Patent No.: US 6,283,969 B1
(45) Date of Patent: Sep. 4, 2001

(54) BONE PLATING SYSTEM

(75) Inventors: N. Kelly Grusin, Memphis, TN (US); Delfreda L. Norman, Mahwah, NJ (US); Maureen Theis-Handwerker, Germantown, TN (US); Andrew J. Weiland, New York, NY (US); Richard H. Gelberman, St. Louis, MO (US); Robert L. Daily, Germantown, TN (US); Gregory S. Fandrich, Easley, SC (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 09/522,088

(22) Filed: Mar. 10, 2000

(51) Int. Cl.⁷ ...................................... A61B 17/56
(52) U.S. Cl. .................. 606/69; 606/71; 606/73
(58) Field of Search .................. 606/69, 70, 71

(56) References Cited

U.S. PATENT DOCUMENTS

| | | | |
|---|---|---|---|
| 3,552,389 | * 1/1971 | Allgower et al. | 606/69 |
| 5,006,120 | 4/1991 | Carter | 606/69 |
| 5,586,985 | * 12/1996 | Putnam et al. | 606/69 |
| 5,931,839 | 8/1999 | Medoff | 606/69 |
| 5,935,128 | 8/1999 | Carter et al. | 606/69 |

* cited by examiner

Primary Examiner—David O. Reip
(74) Attorney, Agent, or Firm—Walker, McKenzie & Walker, P.C.

(57) ABSTRACT

A distal radial plate including a longitudinal segment having a proximal end and a distal end; a transverse segment having a lateral end and a medical end; the distal end of the longitudinal segment attached to the transverse segment intermediate the lateral and medial ends of the transverse segment to form a T-shape; the longitudinal segment having a plurality of spherically recessed holes and having a slot with a proximal end and a distal end; the distal end of the slot having a spherical recess; the proximal end of the slot having a beveled edge which converges distally with the spherical recess of the slot; the transverse segment having a plurality of spherically recessed holes. An extender seats in one of the holes in the transverse segment of the distal radial plate and provides an additional hole on the lateral side of the transverse segment of the plate. Buttress pins have specially formed collars to be secured to the distal radial plate via a "snap-lock." A slotted-style distal radial plate bender has slots for receiving and bending both the transverse and longitudinal segments of the distal radial plate.

4 Claims, 15 Drawing Sheets

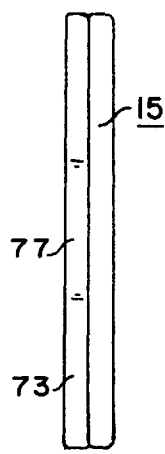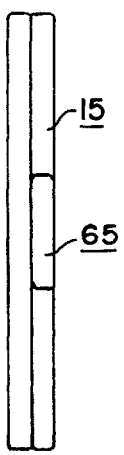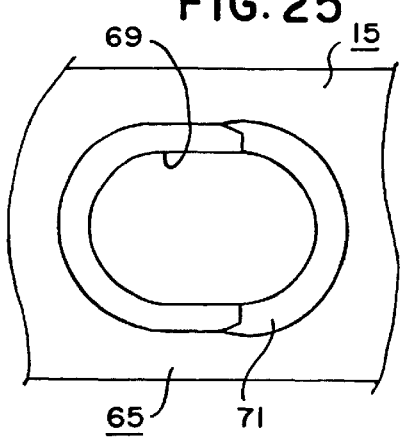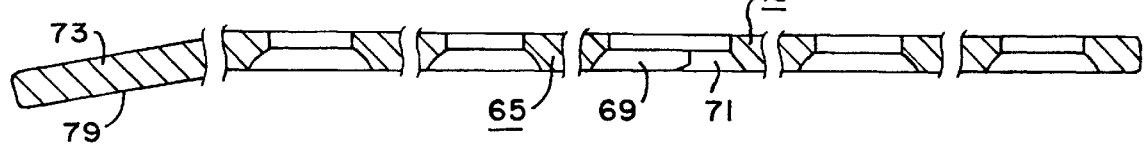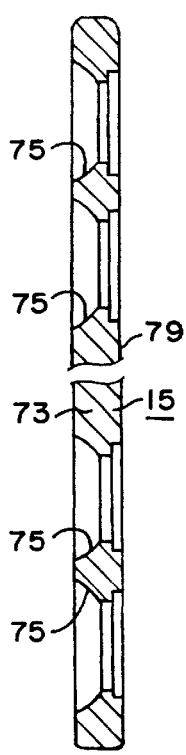

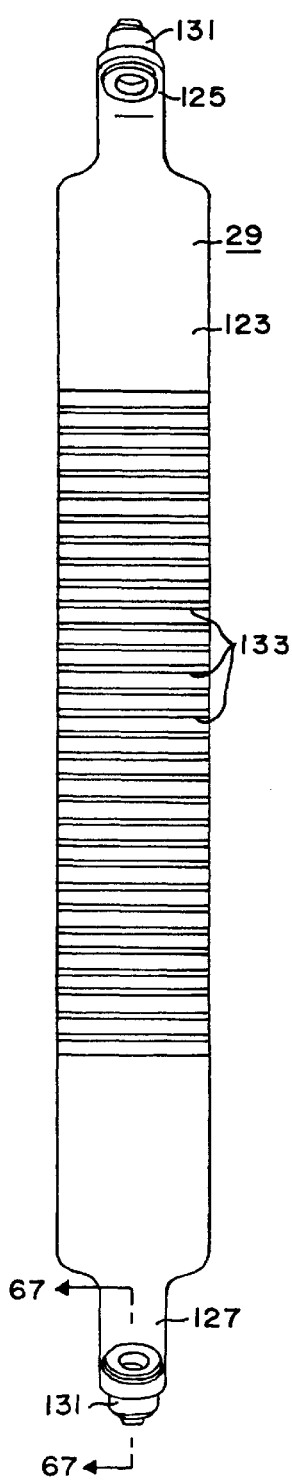
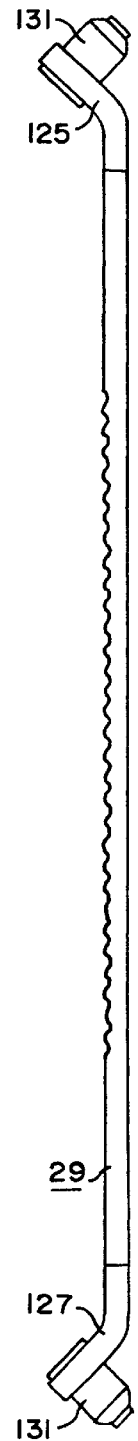
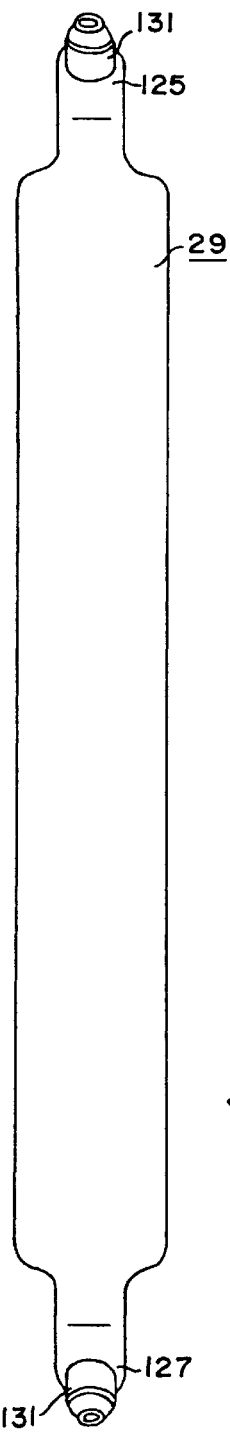
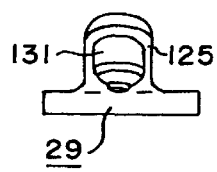
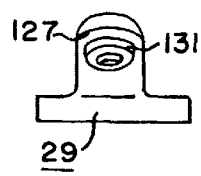
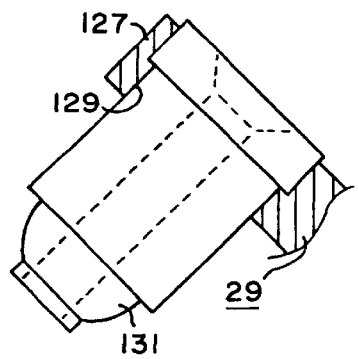

BONE PLATING SYSTEM

CROSS-REFERENCE TO RELATED APPLICATIONS

Not Applicable.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to bone plating systems and, more specifically, to a plating system for fractures of the distal radius.

2. Information Disclosure Statement

Fracture of the distal radius frequently occurs in humans. Such fractures are commonly treated using standard immobilizing cast techniques. Problems associated with such casts including the failure to secure the fracture result in a relatively high rate of deformity, pain, and prolonged disability. External fixation devices utilizing bone pins are used to treat severe distal radial fractures. However, complications, including infection at the pin track sites, joint stiffness, etc., can occur with external fixation devices. Another method used to treat distal radial fractures include surgically exposing the fracture and then using plates, wires, or other internal fixation devices to fix the fracture. However, such internal fixation methods often require a secondary surgery due to tendon irritation and wear caused by the internal devices.

A preliminary patentability search produced the following patents which appear to be relevant to the present invention:

Carter, U.S. Pat. No. 5,006,120, issued Apr. 9, 1991, discloses a bone fixation set for the treatment of distal radial fractures. The set includes a plate having conuntersunk bone screw holes and a bland constructed for placement in the capitate of the radius.

Medoff, U.S. Pat. No. 5,931,839, issued Aug. 3, 1999, discloses an implantable element for fixation of one or more fractured bone fragments to a stable bone fragment. The element includes a pin plate which is fixed to the stable bone fragment by one or more screws, and one or more pins for passing through the pin plate and loose bone fragments, and into the stable bone fragment.

Carter et al., U.S. Pat. No. 5,935,128, issued Aug. 10, 1999, discloses a orthopaedic template system for use with a low profile radius plate.

Nothing in the known prior art discloses or suggests the present invention. For example, nothing in the known prior art discloses or suggests a distal radial plate including a longitudinal segment having a proximal end and a distal end, and a transverse segment having a lateral end and a medial end with the distal end of the longitudinal segment attached to the transverse segment intermediate the lateral and medial ends of the transverse segment to form a T-shape, with the longitudinal segment having a plurality of spherically recessed holes and having a slot with a proximal end and a distal end, with the distal end of the slot having a spherical recess, with the proximal end of the slot having a beveled edge which converges distally with the spherical recess of the slot, and with the transverse segment having a plurality of spherically recessed holes.

BRIEF SUMMARY OF THE INVENTION

The bone plating system of the present invention is designed to give a surgeon a low contour, stainless steel, and volar distal radius plating system for both intra- and extra-articular fractures of the distal radius, while preserving the strength of the current more bulky prior art distal radial plating systems. Other objects of the bone plating system of the present invention is to provide specially designed screws with low profile heads to complement the plates and reduce tendon irritation and wear, provide buttress pins for comminuted fragments that otherwise would not hold a screw; provide an optional lateral extender to obtain fixation of radial styloid fragments; and provide a compression slot for the reduction of extra-articular fractures.

An impetus behind the bone plating system of the present invention is to restore intra-articular congruity while avoiding the need for a secondary surgery due to plate-derived tendon irritation and wear. There is close contact between extensor and flexor tendons and the distal radius shaft. It has been reported that even a slightly damaged screw is mechanically capable of irritation and can be made responsible for a scrub-necrosis. Plates that do not have a low contour or that are too thick can alter the tendons' passage resulting in a second surgery to remove the plate and repair a ruptured tendon. Prior art distal radius plating systems have been shown to cause tendon irritation and/or rupture leading to their subsequent removal. The present invention utilized thin, high strength stainless steel plates with low profile screws to avoid these types of complications.

BRIEF DESCRIPTION OF THE SEVERAL VIEWS OF THE DRAWINGS

FIG. 23 is a distal end view of the volar plate of FIG. 19.

FIG. 24 is a proximal end view of the volar plate of FIG. 19.

FIG. 25 is an enlarged view of a portion of FIG. 19, showing a spherically recessed longitudinal slot thereof.

FIG. 26 is a sectional view substantially as taken on line 26—26 of FIG. 19, on an enlarged scale and with portions thereof broken away for clarity.

FIG. 27 is a sectional view substantially as taken on line 27—27 of FIG. 19, on an enlarged scale and with portions thereof broken away for clarity.

FIG. 62 is a front plan view of a drill guide of the bone plating system of the present invention.

FIG. 63 is a side elevational view of the drill guide of FIG. 62, the other side being substantially a mirror image thereof.

FIG. 64 is a rear plan view of the drill guide of FIG. 62.

FIG. 65 is a top plan view of the drill guide of FIG. 62.

FIG. 66 is a bottom plan view of the drill guide of FIG. 62.

FIG. 67 is a sectional view substantially as taken on line 67—67 of FIG. 62, on a somewhat enlarged scale.

DETAILED DESCRIPTION OF THE INVENTION

Figure 1:
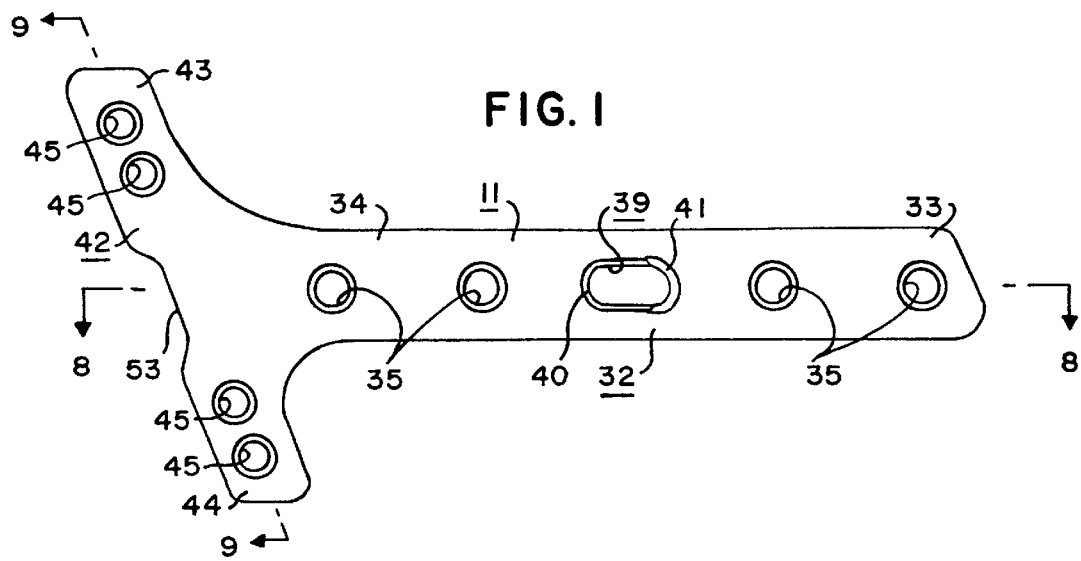
FIG. 1 is a top plan view of a small, left distal radial dorsal plate of the bone plating system of the present invention, the small, right distal radial dorsal plate is a mirror image thereof.
Figure 2:
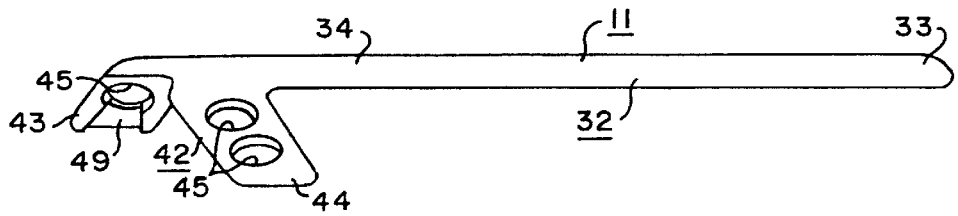
FIG. 2 is a first side elevational view of the dorsal plate of FIG. 1.

The preferred embodiment of the bone plating system of the present invention is used for both intra- and extra-articular fractures of the distal radius, and may include a small, left distal radial dorsal plate as shown generally in FIGS. 1–9 and identified by the numeral 11; a small, right distal radial dorsal plate (shown diagrammatically in FIGS. 68–70, 74 and 75, and being a mirror image of the small, left distal radial dorsal plate 11); a large, left distal radial dorsal plate as shown generally in FIGS. 10–18 and identified by the numeral 13; a large, right distal radial dorsal plate (not shown but being a mirror image of the large, left distal radial dorsal plate 13); a universal distal radial volar plate as shown generally in FIGS. 19–27 and identified by the numeral 15; a distal radial plate extender as shown generally in FIGS. 28–33 and identified by the numeral 17; a buttress pin as shown generally in FIGS. 34–37 and identified by the numeral 19; a buttress pin with soft tissue suture anchor means as shown generally in FIGS. 38–42 and identified by the numeral 21; a buttress pin screw lock pin shank and coacting buttress pin screw lock pin head as shown generally in FIGS. 43–48 and 49–53, respectively, and identified by the numerals 23 and 25, respectively; a slotted plate bender as shown generally in FIGS. 54–61 and identified by the numeral 27; and a drill guide as shown generally in FIGS. 62–67 and identified by the numeral 29.

Figure 3:
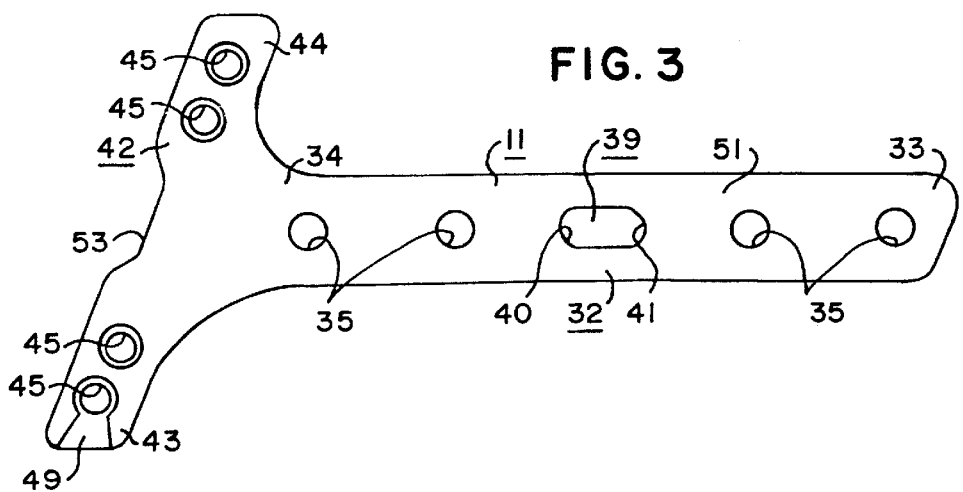
FIG. 3 is a bottom plan view of the dorsal plate of FIG. 1.
Figure 4:
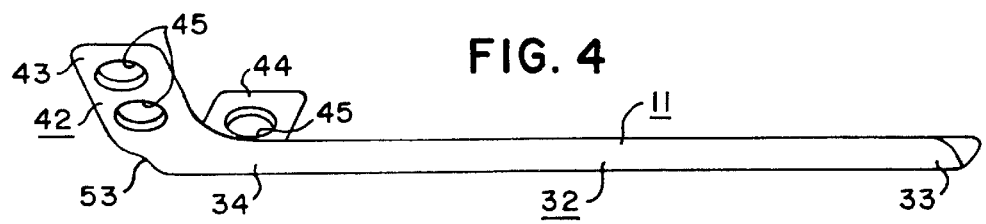
FIG. 4 is a second side elevational view of the dorsal plate of FIG. 1.
Figure 5:
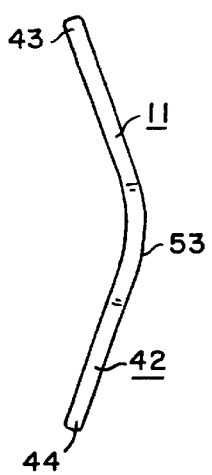
FIG. 5 is a distal end view of the dorsal plate of FIG. 1.
Figure 6:
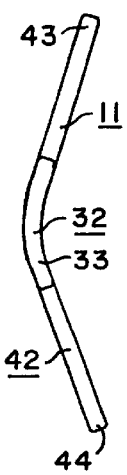
FIG. 6 is a proximal end view of the dorsal plate of FIG. 1.
Figure 7:
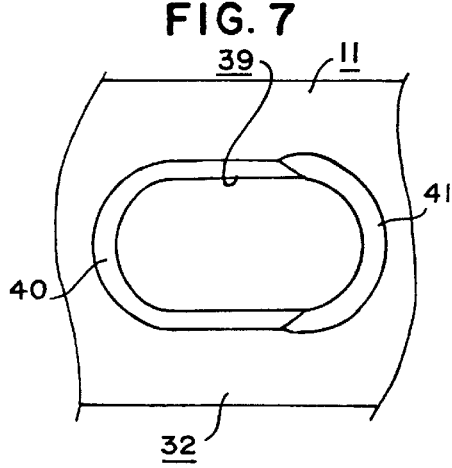
FIG. 7 is an enlarged view of a portion of FIG. 1, showing a spherically recessed longitudinal slot thereof.
Figure 8:
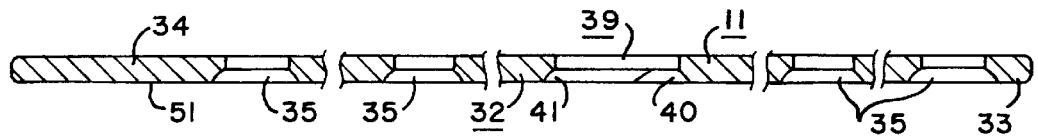
FIG. 8 is a sectional view substantially as taken on line 8—8 of FIG. 1, on an enlarged scale and with portions thereof broken away for clarity.
Figure 9:
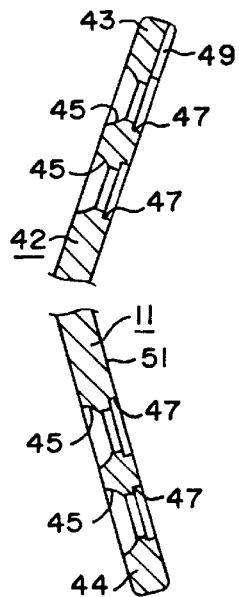
FIG. 9 is a sectional view substantially as taken on line 9—9 of FIG. 1, on an enlarged scale and with portions thereof broken away for clarity.
Figure 10:
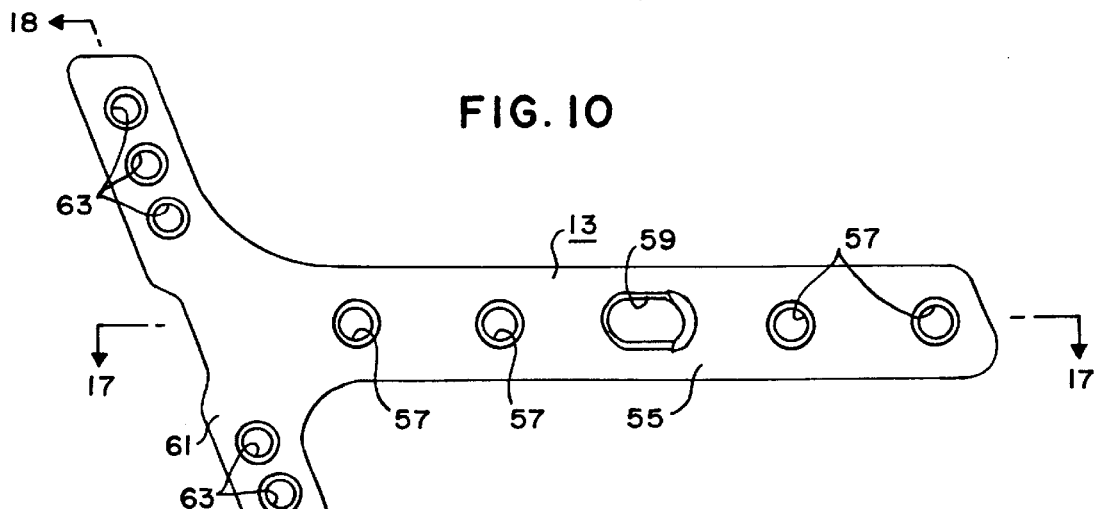
FIG. 10 is a top plan view of a large, left distal radial dorsal plate of the bone plating system of the present invention, the large, right distal radial dorsal plate being a mirror image thereof.
Figure 11:
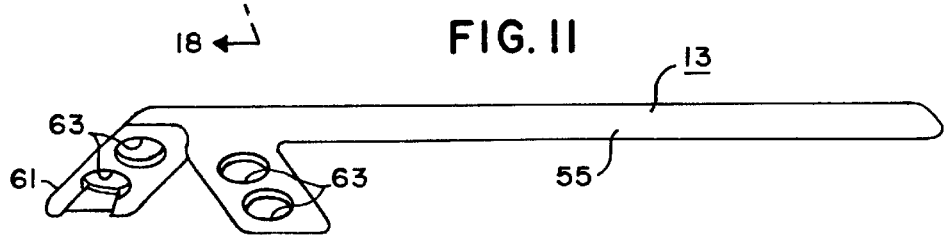
FIG. 11 is a first side elevational view of the dorsal plate of FIG. 10.
Figure 12:
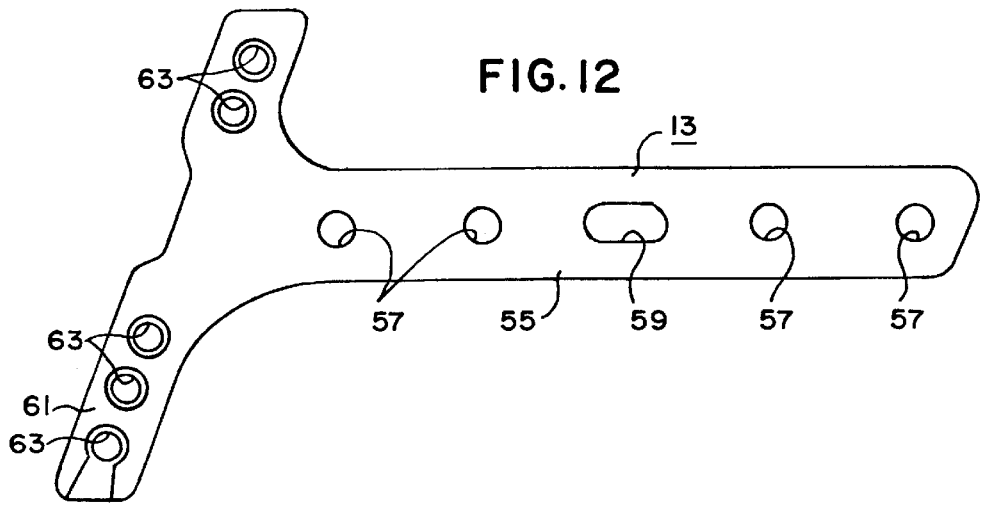
FIG. 12 is a bottom plan view of the dorsal plate of FIG. 10.
Figure 13:
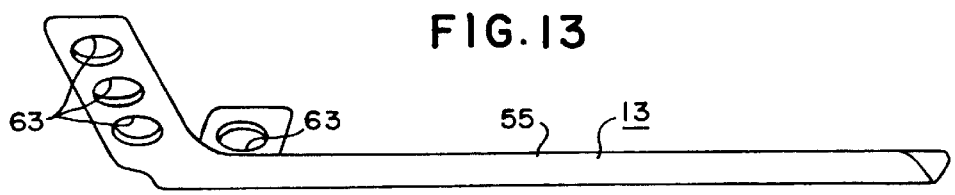
FIG. 13 is a second side elevational view of the dorsal plate of FIG. 10.
Figure 14:
FIG. 14 is a distal end view of the dorsal plate of FIG. 10.
Figure 15:
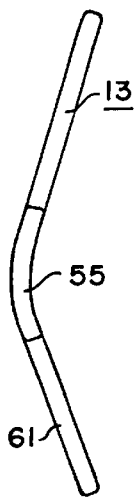
FIG. 15 is a proximal end view of the dorsal plate of FIG. 10.
Figure 16:
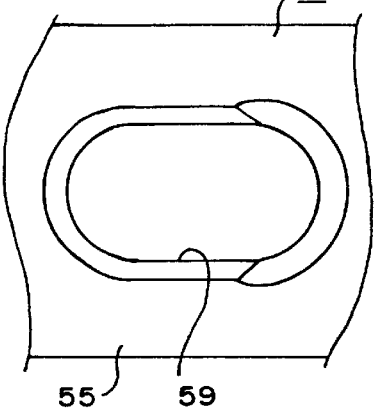
FIG. 16 is an enlarged view of a portion of FIG. 10, showing a spherically recessed longitudinal slot thereof.
Figure 17:
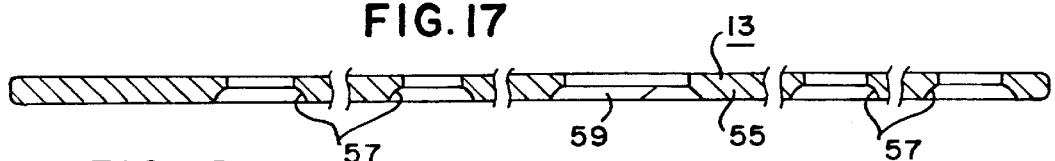
FIG. 17 is a sectional view substantially as taken on line 17—17 of FIG. 10, on an enlarged scale and with portions thereof broken away for clarity.
Figure 18:
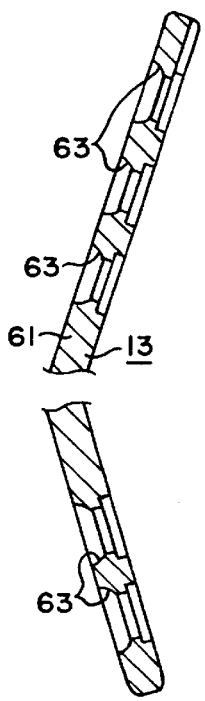
FIG. 18 is a sectional view substantially as taken on line 18—18 of FIG. 10, on an enlarged scale and with portions thereof broken away for clarity.
Figure 76:
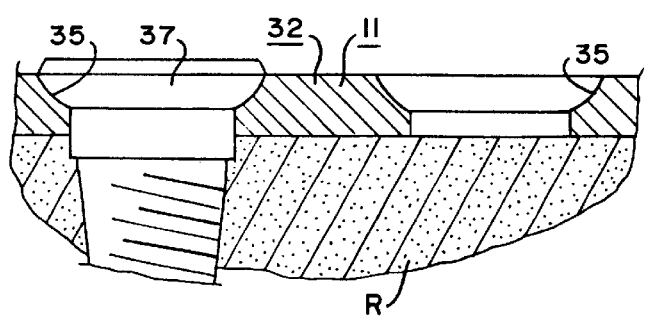
FIG. 76 is a somewhat diagrammatic sectional view of a portion of a longitudinal segment of the small, left distal radial dorsal plate, showing a low profile head bone screw securing the dorsal plate to a radius.
Figure 77:
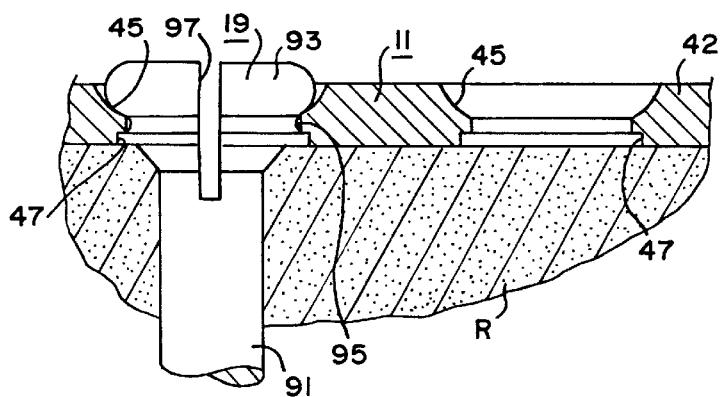
FIG. 77 is a somewhat diagrammatic sectional view of a portion of a transverse segment of the small, left distal radial dorsal plate, showing a buttress pin securing the dorsal plate to a radius.

The small, left distal radial dorsal plate 11 is preferably substantially T-shaped in plan (see, in general, FIGS. 1 and 3). Proximally, the dorsal plate 11 includes a longitudinal segment 32 having a proximal end 33 and a distal end 34. The longitudinal segment 32 preferably has a plurality of spherically recessed holes 35 to accept bone screws 37 (see FIG. 76). This longitudinal segment 32 also has a longitudinal slot 39 for use with bone screws 37 to compress fractures. The longitudinal slot 39 has a distal end 40 and a proximal end 41. The distal end 40 of this slot 39 has a spherical recess. The proximal end 41 of this slot 39 has a beveled edge which converges distally with the spherical edges or recess of the distal end 40 of the slot 39 to create a compression feature so that as a bone screw 37 with a spherical head is seated against this beveled edge, the plate 11 will slide proximally to seat the head of the screw 37 in the spherically recessed distal portion or end 40 of the slot 39. Distally, the dorsal plate 11 includes a transverse segment 42 having a lateral end 43 and a medial end 44. The transverse segment 42 preferably has a plurality of spherically recessed holes 45 to accept buttress pins 19 (see FIG. 77), buttress pins 21, buttress pin screw lock pin shank 23 and pin head 25 combinations, and/or bone screws 37. The holes 45 preferably have a counterbore 47 on the bottom side of the plate 11 in order to create a locking feature for the buttress pins 19, buttress pins 21, and/or buttress pin screw lock pin shank 23 and pin head 25 combinations. The transverse segment 42 preferably has a transverse, recessed slot 49 connected to the hole 45 on the lateral end 43 of this transverse segment 42, on the bottom face 51 of the plate 11 and which extends laterally from this last hole 45, increasing in width, through the lateral end 43 of the transverse segment 42. This slot 49 is used for the addition of an extender 17 which when inserted in this slot 49 can be angled 15 degrees either proximally or distally. This distal transverse segment 42 of the plate 11 also preferably has a central divot 53 which allows visualization of the distal radius articulating surface and in part provides a relief for Lister's Tubercle. The transverse segment 42 of the plate 11 is preferably angled with respect to the longitudinal segment 32 to further match the anatomy of the distal radius R (see, in general, FIGS. 68 and 74). The plate 11 is preferably pre-bent to approximately a 140° angle (see, in general, FIGS. 5 and 6) so that its bottom face 51 conforms as closely as possible to the surface of the distal radius R (see, in general, FIGS. 69 and 70). The plate 11 preferably has a low profile and smooth finish so as to minimize tendon irritation. The plate 11 is preferably constructed of a surgical grade stainless steel. More specifically, based on the strength necessary and the clinical history of other currently marketed distal radial plating systems, high strength 316L stainless steel is preferably used to construct the plate 11 to allow the plate 11 to be constructed as thin as possible and the thinnest material possible without sacrificing strength, and to provide pliability of the plate 11 for precise fitting.

As indicated hereinabove, the small, right distal radial dorsal plate is a mirror image of the small, left distal radial dorsal plate 11, and the above disclosure of the small, left distal radial dorsal plate 11 will provide a full and enabling teaching of the small, right distal radial dorsal plate to one of ordinary skill in the art. The small, right distal radial dorsal plate is shown diagrammatically in FIGS. 68–70, 74 and 75, with like features identified with the same reference numbers as used for the small, left distal radial dorsal plate 11.

Other than size and one exception discussed hereinbelow, the large, left distal radial dorsal plate 13 is preferably identical in design and construction to the small, left distal radial dorsal plate 11, and is preferably substantially T-shaped in plan (see, in general, FIGS. 10 and 12), with a proximal longitudinal segment 55, a plurality of spherically recessed holes 57 and a spherically recessed longitudinal slot 59 in the proximal longitudinal segment 55, a distal transverse segment 61, a plurality of spherically recessed holes 63 in the distal transverse segment 61, etc. The above disclosure of the corresponding features, etc., of the small, left distal radial dorsal plate 11 will provide a full and enabling teaching of such features, etc., for the large, left distal radial dorsal plate to one of ordinary skill in the art. The one exception mentioned hereinabove is that in the large, left distal radial dorsal plate 13, the lateral end of the distal transverse segment 61 is extended proportionally a greater distance from the proximal longitudinal segment 55 than the lateral end 43 of the distal transverse segment 42 is extended from the proximal longitudinal segment 32 of the small, left distal radial dorsal plate 11, and an additional spherically recessed hole 63 is provided through the lateral end 43 of the distal transverse segment 42.

As indicated hereinabove, the large, right distal radial dorsal plate is a mirror image of the large, left distal radial dorsal plate 13, and the above disclosure of the large, left distal radial dorsal plate 13 will provide a full and enabling teaching of the large, right distal radial dorsal plate to one of ordinary skill in the art.

Figure 19:
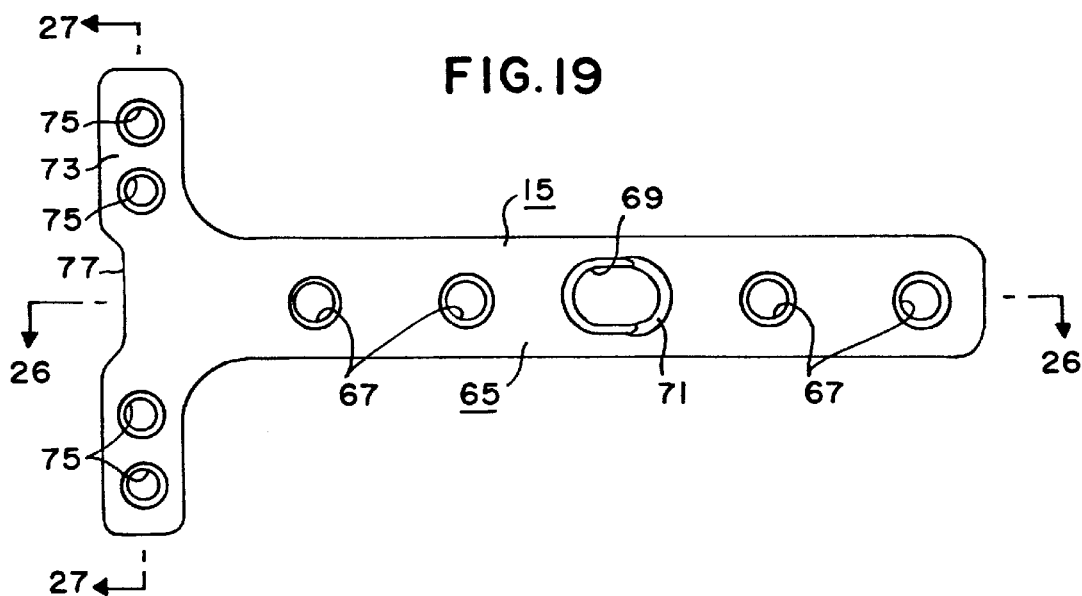
FIG. 19 is a top plan view of a universal distal radial volar plate of the bone plating system of the present invention.
Figure 20:
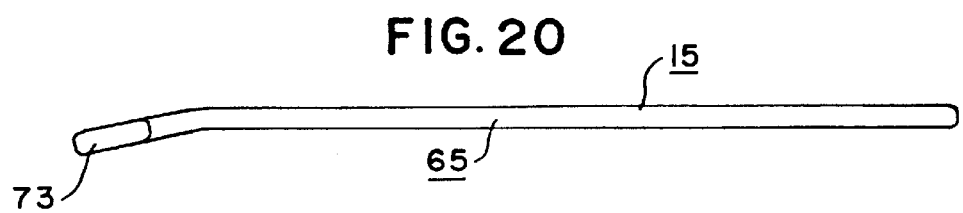
FIG. 20 is a first side elevational view of the volar plate of FIG. 19.
Figure 21:
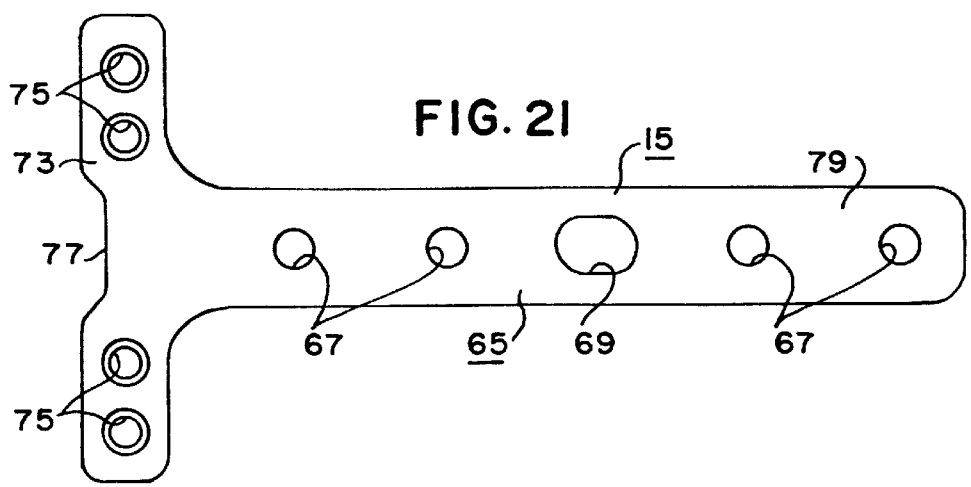
FIG. 21 is a bottom plan view of the volar plate of FIG. 19.
Figure 22:
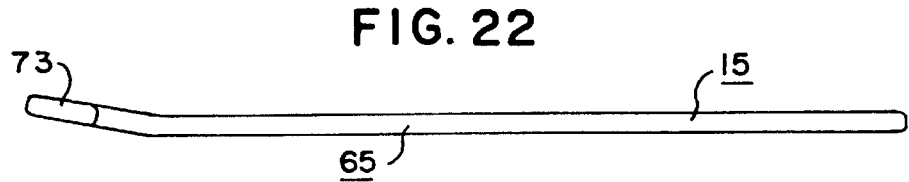
FIG. 22 is a second side elevational view of the volar plate of FIG. 19.
Figure 28:
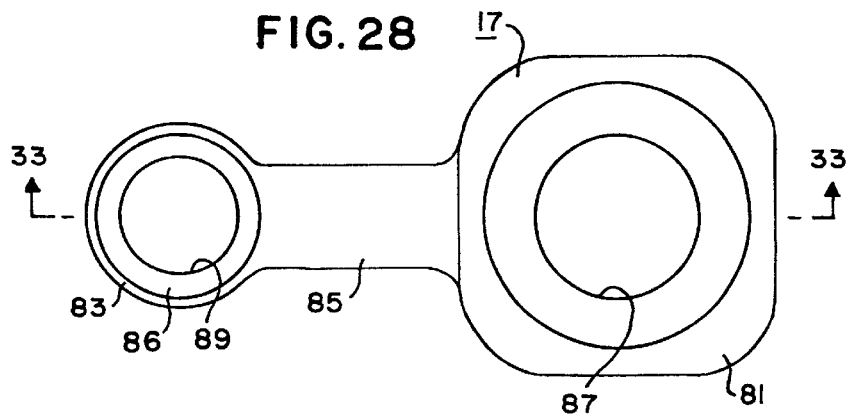
FIG. 28 is as a top plan view of a distal radial plate extender of the bone plating system of the present invention.
Figure 29:
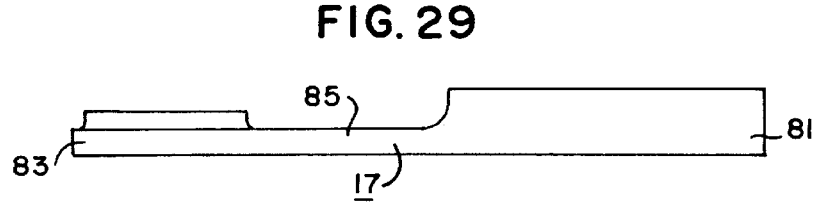
FIG. 29 is a first side elevational view of the distal radial plate extender of FIG. 28, the second side being a mirror image thereof.
Figure 30:
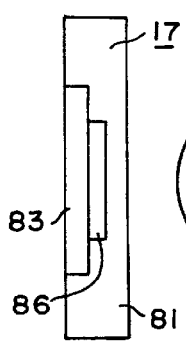
FIG. 30 is a first end view of the distal radial plate extender of FIG. 28.
Figures 31, 32:
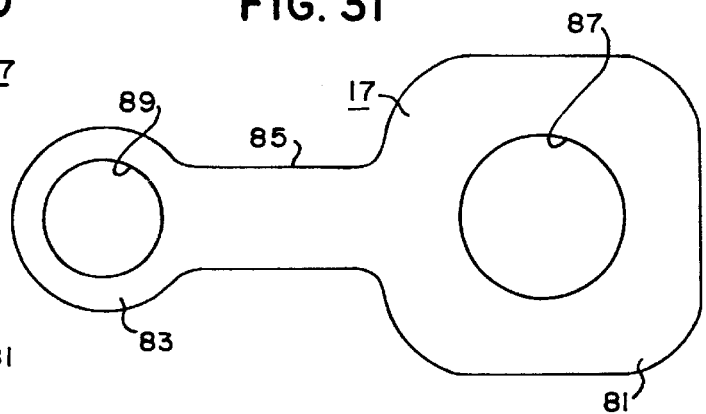
FIG. 31 is a bottom plan view of the distal radial plate extender of FIG. 28.
FIG. 32 is a proximal end view of the distal radial plate extender of FIG. 28.
Figure 33:
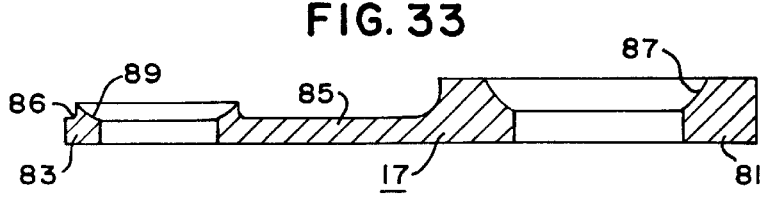
FIG. 33 is a sectional view substantially as taken on line 33—33 of FIG. 28.
Figure 34:
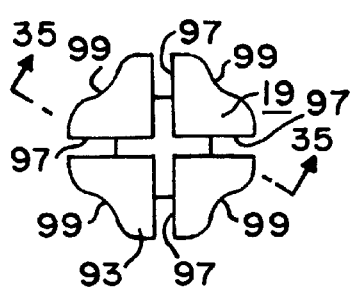
FIG. 34 is a top plan view of a buttress pin of the bone plating system of the present invention.
Figure 35:
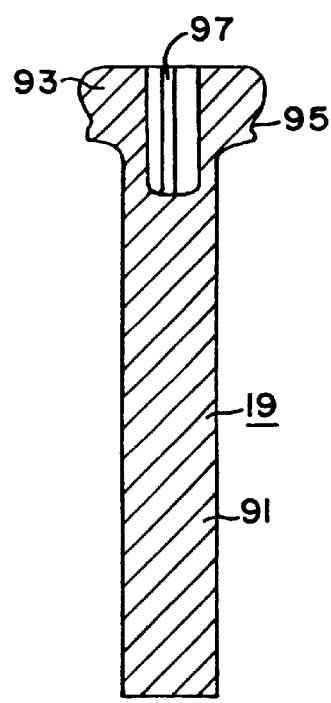
FIG. 35 is a sectional view substantially as taken on linen 35—35 of FIG. 34.
Figure 36:
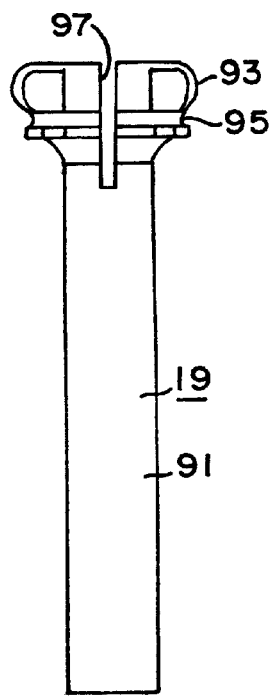
FIG. 36 is a front elevational view of the buttress pin of FIG. 34, the rear and side elevational views being substantially mirror images thereof.
Figure 37:
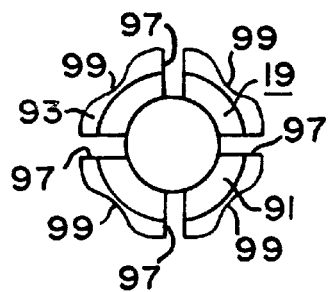
FIG. 37 is a bottom plan view of the buttress pin of FIG. 34.
Figure 38:
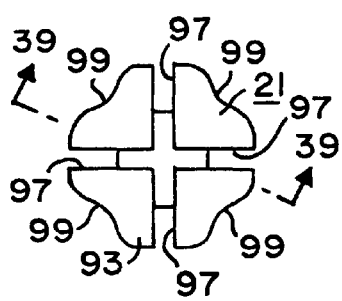
FIG. 38 is a top plan view of a buttress pin with soft tissue suture anchor means of the bone plating system of the present invention.
Figure 39:
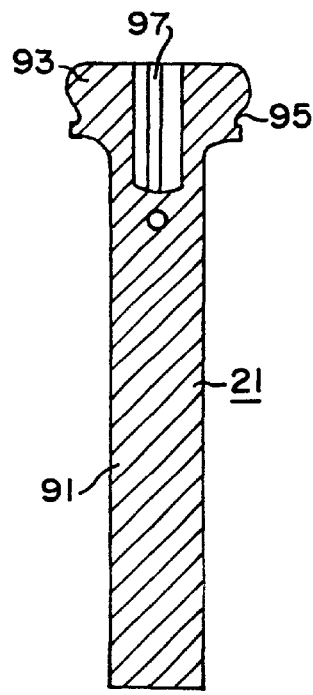
FIG. 39 is a sectional view substantially as taken on line 39—39 of FIG. 38.
Figure 40:
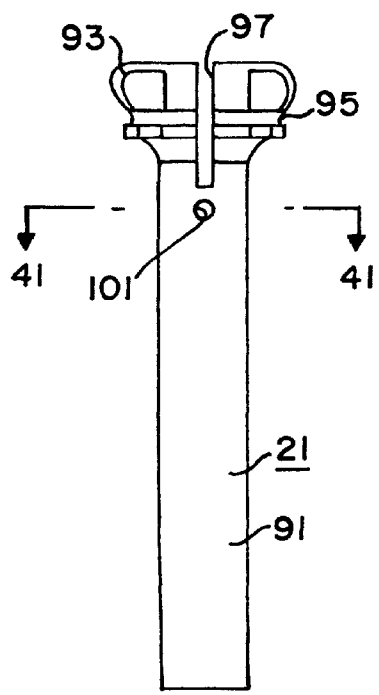
FIG. 40 is a front elevational view of the buttress pin of FIG. 38, the rear and side elevational views being substantially mirror images thereof.
Figure 41:
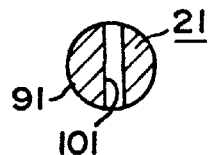
FIG. 41 is a sectional view substantially as taken on line 41—41 of FIG. 40.
Figure 42:
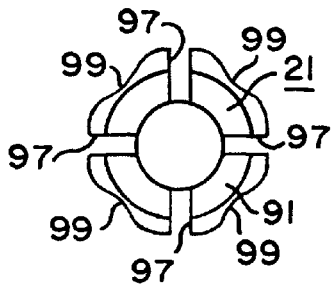
FIG. 42 is a bottom plan view of the buttress pin of FIG. 38.
Figure 43:
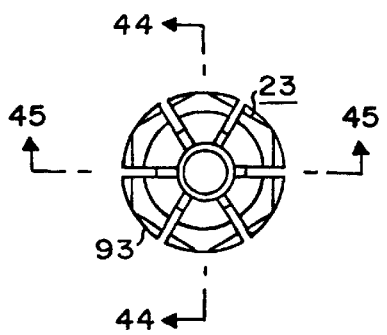
FIG. 43 is a top plan view of a buttress pin screw lock pin shank of the bone plating system of the present invention.
Figure 44:
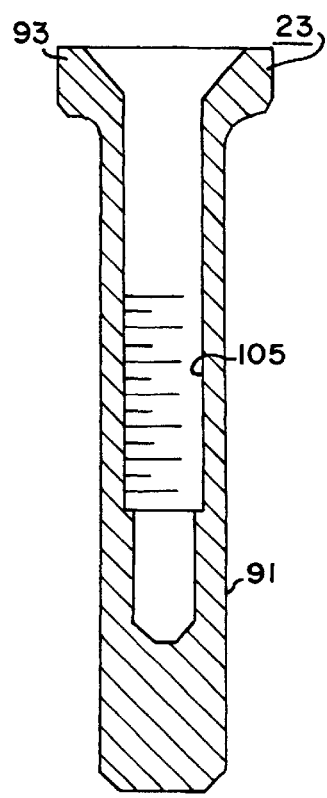
FIG. 44 is a sectional view substantially as taken on line 44—44 of FIG. 43.
Figure 45:
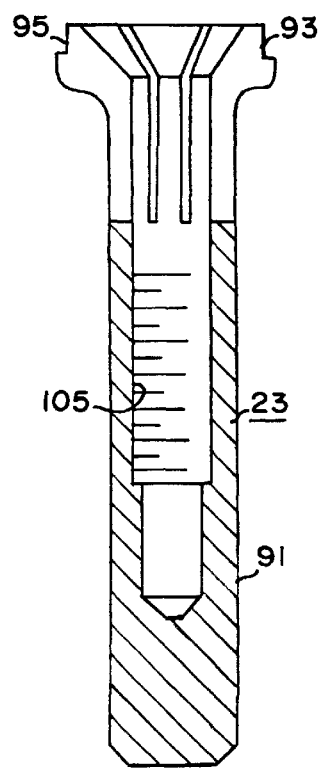
FIG. 45 is a sectional view substantially as taken on line 45—45 of FIG. 43.
Figure 46:
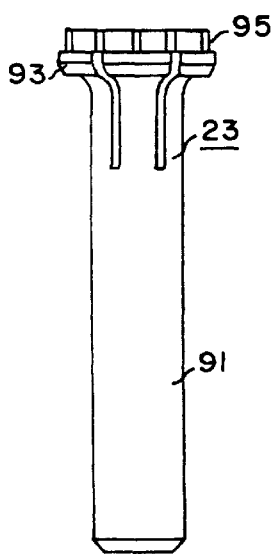
FIG. 46 is a front elevational view of the screw lock pin shank of FIG. 43, the rear and side elevational views being substantially mirror images thereof.
Figure 48:
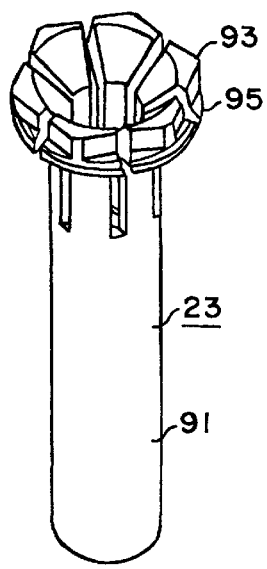
FIG. 48 is a perspective view of the screw lock pin shank of FIG. 43.
Figure 47:
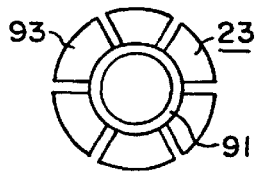
FIG. 47 is a bottom plan view of the screw lock pin shank of FIG. 43.
Figure 49:
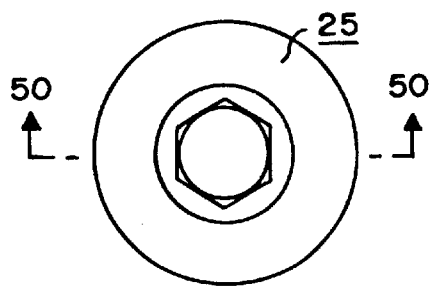
FIG. 49 is a top plan view of a buttress pin screw lock pin head of the bone plating system of the present invention.
Figure 50:
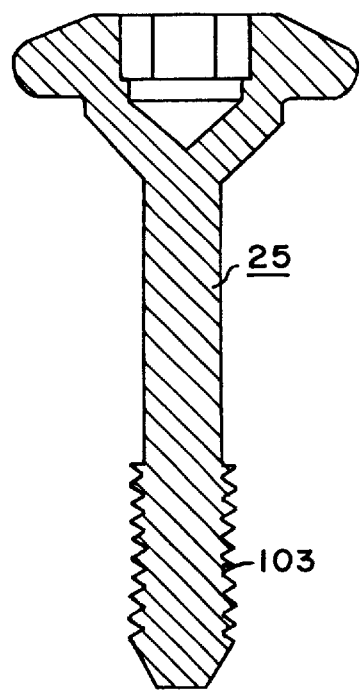
FIG. 50 is a sectional view substantially as taken on line 50—50 of FIG. 49.
Figure 51:
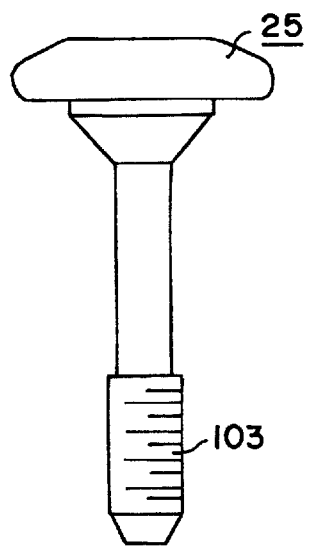
FIG. 51 is a front elevational view of the screw lock pin head of FIG. 49, the rear and side elevational views being substantially mirror images thereof.
Figure 53:
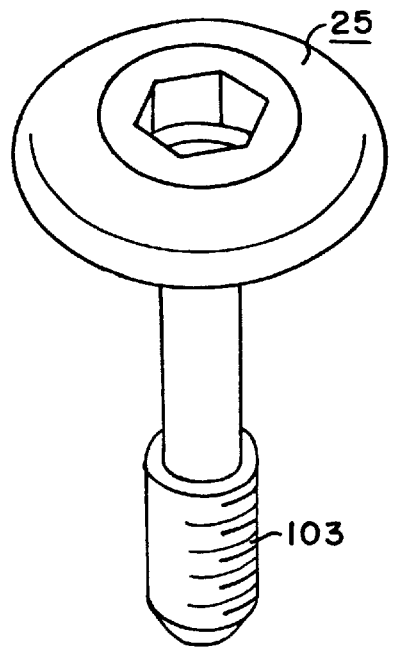
FIG. 53 is a perspective view of the screw lock pin head of FIG. 49.
Figure 52:
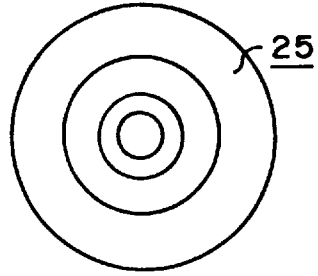
FIG. 52 is a bottom plan view of the screw lock pin head of FIG. 49.
Figure 54:
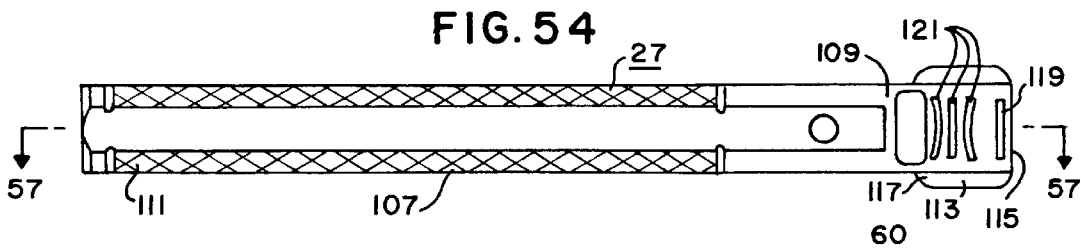
FIG. 54 is a top plan view of a slotted plate bender of the bone plating system of the present invention.
Figure 55:
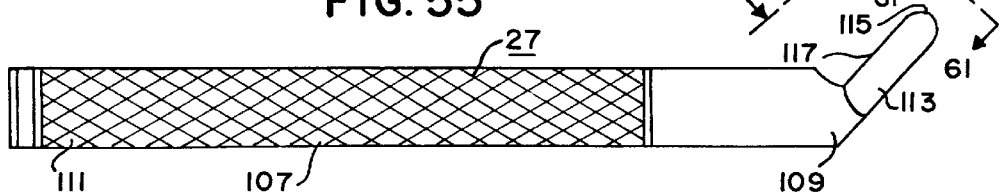
FIG. 55 is a side elevational view of the slotted plate bender of FIG. 54, the other side being a mirror image thereof.
Figure 56:
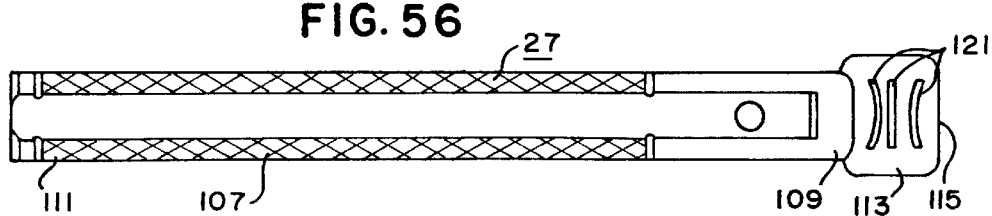
FIG. 56 is a bottom plan view of the slotted plate bender of FIG. 54.
Figure 57:
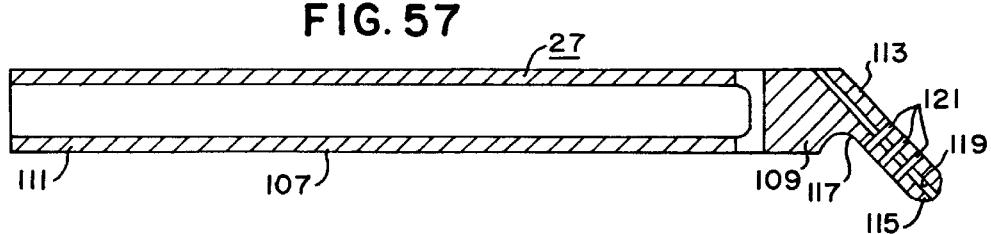
FIG. 57 is a sectional view substantially as taken on line 57—57 of FIG. 54.
Figure 58:
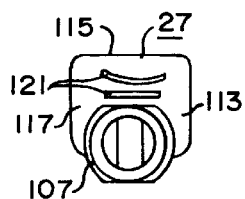
FIG. 58 is a left end view of the slotted plate bender of FIG. 54.
Figure 59:
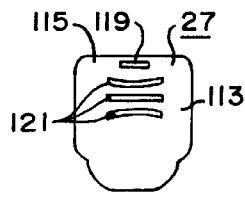
FIG. 59 is a right end view of the slotted plate bender of FIG. 54.
Figure 60:
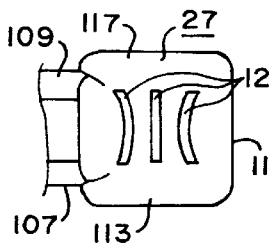
FIG. 60 is a normal view of a portion of the slotted plate bender of FIG. 54, substantially as taken on line 60—60 of FIG. 55 on a somewhat enlarged scale.
Figure 61:
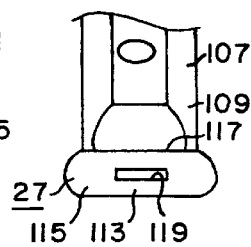
FIG. 61 is a normal view of a portion of the slotted plate bender of FIG. 54, substantially as taken on line 61—61 of FIG. 55 on a somewhat enlarged scale.
Figure 68:
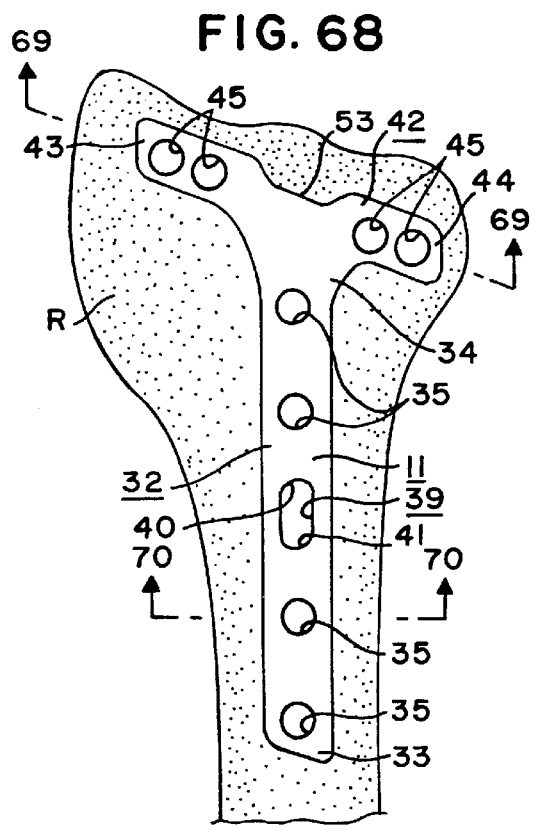
FIG. 68 is a somewhat diagrammatic dorsal view of the distal end of a radius, showing a small, right distal radial dorsal plate of the bone plating system of the present invention attached thereto, with parts thereof omitted for clarity.
Figure 69:
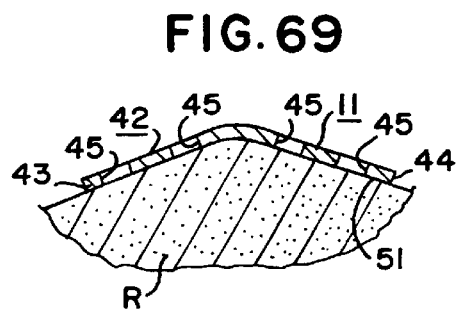
FIG. 69 is a somewhat diagrammatic sectional view substantially as taken on line 69—69 of FIG. 68, with portions thereof broken away for clarity.
Figure 70:
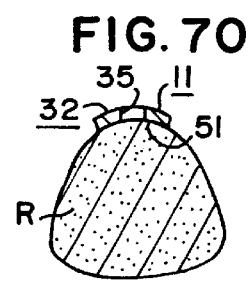
FIG. 70 is a somewhat diagrammatic sectional view substantially as taken on line 70—70 of FIG. 68, with portions thereof omitted for clarity.
Figure 71:
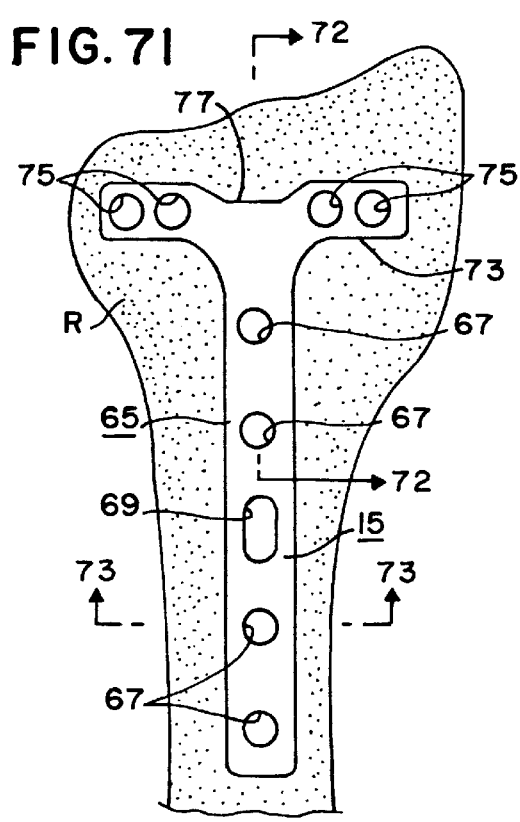
FIG. 71 is a somewhat diagrammatic volar view of the distal end of a radius, showing a universal distal radial volar plate of the bone plating system of the present invention attached thereto, with parts thereof omitted for clarity.
Figure 72:
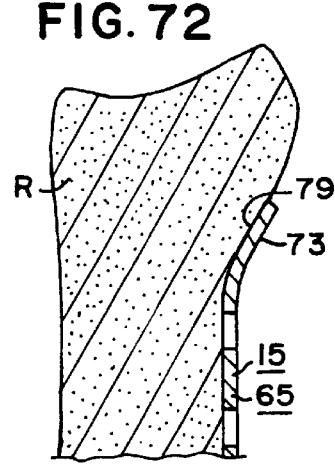
FIG. 72 is a somewhat diagrammatic sectional view substantially as taken on line 72—72 of FIG. 71.
Figure 73:
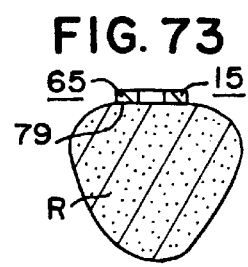
FIG. 73 is a somewhat diagrammatic sectional view substantially as taken on line 73-71 of FIG. 71, with portions thereof omitted for clarity.
Figure 74:
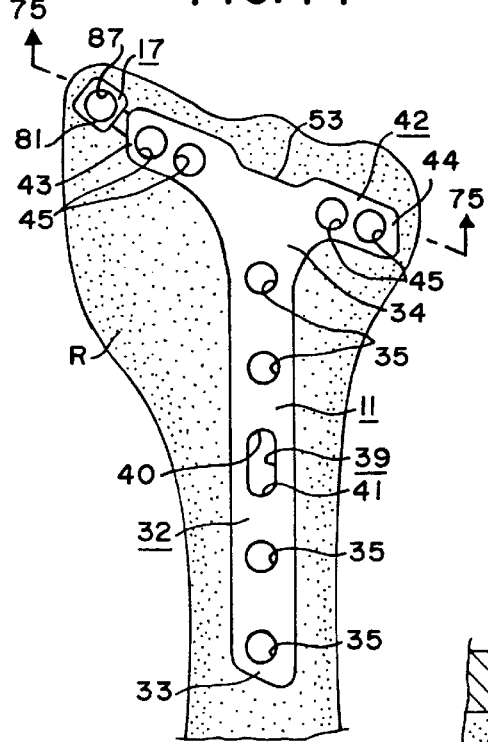
FIG. 74 is a somewhat diagrammatic dorsal view of the distal end of a radius, showing a small, right distal radial dorsal plate and a distal radial plate extender of the bone plating system of the present invention attached thereto, with parts thereof omitted for clarity.
Figure 75:
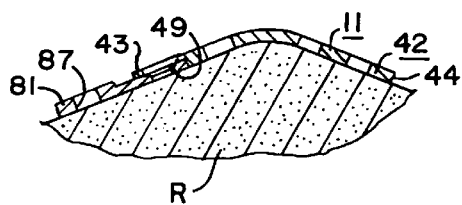
FIG. 75 is a somewhat diagrammatic sectional view substantially as taken on line 75—75 of FIG. 74, with portions thereof broken away for clarity.

The universal distal radial volar plate 15 is preferably substantially T-shaped in plan (see, in general, FIGS. 19 and 21). Proximally, the volar plate 15 includes a longitudinal segment 65 preferably having a plurality of spherically recessed holes 67 to accept bone screws 37. This longitudinal segment 65 also has a spherically recessed longitudinal slot 69 for use with bone screws 37 to compress fractures. The proximal end 71 of this slot 69 has a beveled edge which converges distally with the spherical edges of the slot 69 to create a compression feature so that as a bone screw 37 with a spherical head is seated against this beveled edge, the plate 15 will slide proximally to seat the head of the screw 37 in the spherically recessed portion of the slot 69. Distally, the volar plate 15 includes a transverse segment 73 preferably having a plurality of spherically recessed holes 75 to accept buttress pins 19, buttress pins 21, buttress pin screw lock pin shank 23 and pin head 25 combinations, and/or bone screws 37. The holes 75 preferably have a counterbore 47 on the bottom side of the plate 11 in order to create a locking feature for the buttress pins 19, buttress pins 21, and/or buttress pin screw lock pin shank 23 and pin head 25 combinations. This distal transverse segment 73 of the plate 15 also preferably has a central divot 77. The distal end of the plate 15 is preferably pre-bent to approximately a 155° angle (see, in general, FIGS. 20 and 22) so that its bottom face 79 conforms as closely as possible to the surface of the distal radius R (see, in general, FIG. 72). The plate 15 preferably has a low profile and smooth finish so as to minimize tendon irritation. The plate 15 is preferably constructed of a surgical grade stainless steel. More specifically, based on the strength necessary and the clinical history of other currently marketed distal radial plating systems, high strength 316L stainless steel is preferably used to construct the plate 15 to allow the plate 15 to be constructed as thin as possible and the thinnest material possible without sacrificing strength, and to provide pliability of the plate 15 for precess fitting. The volar plate 15 is not side specific and may be offered in only one size.

The distal radial plate extender 17 mates with the bottom side of, e.g., the small, left distal radial dorsal plate 11 (or the large, left distal radial dorsal plate 13, or the small or large right distal radial dorsal plates) to provide an additional hole on the lateral side of the head or transverse segment 42 of the dorsal plate 11, etc. The extender 17 preferably has a first end 81, a second end 83, and a midportion 85 joining the first and second ends 81, 83. The second end 83 has a boss portion 86 sized to extend into and seat in the most distal spherically recessed hole 45 in the dorsal plate 11, with the midportion 85 located in the transverse, recessed slot 49, etc. The distal radial plate extender 17 preferably has a first spherically recessed hole 87 in the first end 81 thereof and a second spherically recessed hole 89 in the second end 83 thereof. The distal radial plate extender 17 eliminates the trimming and filing debris associated with an attached hole found in other systems. Connection of the distal radial plate extender 17 through the transverse, recessed slot 49 allows angulation of the distal radial plate extender 17 for better proximal/distal position of the extender hole 87. The distal radial plate extender 17 is preferably constructed out of stainless steel.

The buttress pins 19, 21 and buttress pin combination 23, 25 are for use with a fracture fixation plate, specifically a distal radial dorsal or volar plate as disclosed herein, for the positioning of small bone fragments (the following description of the buttress pins 19, 21 and buttress pin combination 23, 25 will be in combination with the small, left distal radial dorsal plate 11 but it should be understood that the buttress pin 19, 21 and buttress pin combination 23, 25 are not limited for use with the small, left distal radial dorsal plate 11). Each buttress pin 19, 21 and the buttress pin screw lock pin shank 23 includes a shank 91 for extending through one of the spherically recessed holes 45 in the transverse segment 42 of the distal radial dorsal plate 11, and into a bone fragment of the distal radius R (see, for example, FIG. 77). Each buttress pin 19, 21 and the buttress pin screw lock pin shank 23 includes a collar 93 attached to the shank 91 for locking the distal radial dorsal plate 11 to the corresponding buttress pin 19, 21 or buttress pin screw lock pin shank 23. The collar 93 has a recessed groove 95 thereabout and is movable between a first position for allowing the collar 93 to be inserted into one of the spherically recessed holes 45 in the transverse segment 42 of the distal radial dorsal plate 11, and a second position in which the recessed groove 95 of the collar 93 captures at least a portion of the edge of that spherically recessed hole 45 in the transverse segment 42 of the distal radial dorsal plate 11 to lock the distal radial dorsal plate 11 and the corresponding buttress pin 19, 21 or buttress pin screw lock pin shank 23 together. The head or collar 93 will thus interlock with the hole 45 vial a "snap-lock." The collar 93 of the buttress pins 19, 21 may have a slot 97 (preferably a pair of intersecting slots 97 as clearly shown in FIGS. 34 and 38) therein to allow the collar 93 to be compressed to the first position when inserted into a spherically recessed hole 45 in the transverse segment 42 of the distal radial dorsal plate 11 and to expand or spring back to the second position with the recessed groove 95 of the collar 93 capturing at least a portion of the edge of that spherically recessed hole 45 in the transverse segment 42 of the distal radial dorsal plate 11. The collar 93 of the buttress pins 19, 21 may have a plurality of divots 99 (preferably four opposing divots 99) for allowing the collar 93 to be compressed from the second position to the first position (I.e., for use in the compression and removal of the pins 19, 21 from the distal radial dorsal plate 11). The buttress pin 21 includes means for allowing the pin to be attached to soft tissue. More specifically, the buttress pin 21 preferably has a hole 101 through the shank 91 thereof just beneath the collar 93 thereof for allowing a suture to extend therethrough to attach the buttress pin 21 to soft tissue. The buttress pin screw lock pin head 25 is designed to extend into at least the collar 93 of the buttress pin screw lock pin shank 23 to cause that collar 93 to move from the first position to the second position. The buttress pin screw lock pin head 25 preferably has a male screw portion 103, and the buttress pin screw lock pin shank 23 preferably has a internally threaded aperture 105 in the collar 93 and shank 91 thereof for receiving the screw portion 103 whereby screwing the screw portion 103 into the internally threaded aperture 105 causes the collar 93 to expand from the first position to the second position. The buttress pin screw lock pin shank 23 is first inserted into the desired hole 45 in the transverse segment 42 of the distal radial dorsal plate 11 until the collar 93 thereof "snaps-in" the hole 45 and the screw lock pin head 25 is then screwed into the screw lock pin shank 23 and tightened, causing the collar 93 to expand and locking the unit ( the buttress pin combination 23, 25 and the distal radial dorsal plate 11) together in a very solid connection. The buttress pins 19, 21 and buttress pin combination 23, 25 are preferably constructed out of stainless steel.

The slotted plate bender 27 is designed for use in bending and molding a fracture fixation plate to match the anatomy of a specific radius R. The plate bender 27 is specifically designed for use with a distal radial dorsal or volar plate as disclosed herein and the following description of the plate bender 27 will be in combination with the small, left distal radial dorsal plate 11 but it should be understood that the plate bender 27 is not limited for use with the small, left distal radial dorsal plate 11. The plate bender 27 includes an elongated, preferably round, handle 107 having a first end 109 and a second end 111. The plate bender 27 includes a tip 113 attached to the first end 109 of the elongated handle 107 at an angle thereto. The tip 113 has an end surface 115 and a face surface 117 substantially perpendicular to the end surface 115. The tip 113 has a first slot 119 extending through the end surface 115 for receiving an end of the transverse segment 42 of the plate 11, and has a plurality of slots 121 extending through the face surface 117 thereof for receiving an end of the longitudinal segment 32 of the plate 11, or the longitudinal segment 65 or transverse segment 73 of the volar plate 15. The angled tip 113, in combination with the elongated handle 107, provides leverage for bending the plate 11. At least portions of the surface of the handle 107 may be knurled or otherwise formed to provide a secure grip. The plate bender 27 is preferably constructed out of stainless steel.

The drill guide 29 shown in FIGS. 62–67 includes an elongated, substantially flat body 123 having an upturned first end 125 and an upturned second end 127 Each end 125, 127 has an aperture 129 therethrough to allow a drill guide tip 131 to be inserted thereinto. Grooves 133 may be provide on the surface of the body 123 to allow the surgeon to securely grip the drill guide 29. The drill guide tips 131 are provided in various sizes depending on the size of screw, buttress pin, etc., to be used.

Operative exposure of a distal radial fracture becomes necessary if acceptable reduction cannot be achieved by closed means in those high-energy injuries in which extensive soft tissue or associated skeletal injury requires stable fixation of the distal radius.

To use the bone plating system of the present invention with a dorsal approach, typically a straight longitudinal incision is made over the dorsal radius between the second and third dorsal extensor compartments and extending between 7 and 12 centimeters. The fracture can then be identified and exposed, and the structures retracted on both sides of the distal radial shaft. At that time, under direct vision, the fracture can be confirmed, reduced and/or brought out to length with distraction to verify this. After ensuring reduction through distraction or manual manipulations and with fluoroscopic X-rays, the surgeon can then decide what size plate 11, 13, etc., to use and if an extender 17 will be needed due to any floating radial styloid fragments. A malleable template of the selected plate 11, 13, etc., can then be placed and used to determine the appropriate contour of the fractured radius R. Removal of the Lister's tubercle may be necessary. The bender 27 can then be used to match the selected plate 11, 13, etc., to the contoured template. Care should be taken not to bend the selected plate 11, 13, etc., across the holes 45, etc., designed for use with buttress pins 19, 21 or buttress pin combinations 23, 25. Appropriate screw size as well as screw and pin placement can then be determined. Screw and pin holes must be predrilled in the radius R with the appropriate drill and drill guide 29. The screws should be self-tapping and can be inserted directly into their corresponding drilled holes. The buttress pins 19, 21 or buttress pin combinations 23, 25 will interlock with the plate 11, etc., once inserted into their corresponding drilled holes. A firm push on the head of the buttress pin 19, 21 or buttress pin combination 23, 25 will "snap" the head into the plate 11, etc. Note: the buttress pins 19, 21 and buttress pin combinations 23, 25 are designated for the holes 45 in the transverse segment 42 of the plate 11, etc. Additionally, the buttress pins 19, 21 and buttress pin combinations 23, 25 are not to be used to either attach the extender 17 to the plate 11, etc., or with the hole 89 in the extender 17. If compression of the fracture is necessary, the compression slot 39 in the middle of the longitudinal segment 32 of the plate 11, etc., may be used. A hole is drilled at the proximal end 41 of the slot 39, etc., so that as a screw is seated against the proximal end 41 of the slot 39, the head of the screw will pull the entire plate proximally.

To use the bone plating system of the present invention with a palmar approach, an appropriate surgical approach is used with regard to the anterior aspect of the distal radius to provide adequate exposure while protecting the median and ulnar nerves, flexor tendons, and palmar capsular radiocarpal ligaments. The fracture can then be identified and exposed, and the structures are retracted on both sides of the distal radial shaft. Then, under direct vision, the fracture is confirmed, reduced and/or brought out to length with distraction to verify this. After ensuring reduction through distraction or manual manipulation and with fluoroscopic X-rays, a surgeon can then place and contour the volar plate 15. Care should be taken not to bend the volar plate 15 across the holes 75 designated for use with buttress pins. Attachment of the plate 15 with screws and buttress pins, etc., can follow the same procedures described hereinabove relative to the dorsal approach.

Although the present invention has been described and illustrated with respect to a preferred embodiment and a preferred use therefor, it is not to be so limited since modifications and changes can be made therein which are within the full intended scope of the invention.

What is claimed is:

1. A distal radial plate for the fixation of a fractured distal radius, said distal radial plate comprising:

(a) a longitudinal segment having a proximal end and a distal end; and (b) a transverse segment having a lateral end and a medial end;

said distal end of said longitudinal segment attached to said transverse segment intermediate said lateral and medial ends of said transverse segment to form a T-shape;

said longitudinal segment having a plurality of spherically recessed holes and having a slot with a proximal end and a distal end; said distal end of said slot having a spherical recess; said proximal end of said slot having a beveled edge which converges distally with the spherical recess of said slot;

said transverse segment having a plurality of spherically recessed holes;

each of said spherically recessed holes of said transverse segment having a counterbore.

2. The distal radial plate of claim 1 in which said transverse segment has a recessed slot extending from said lateral end thereof to one of said spherically recessed hole of said transverse segment.

3. The distal radial plate of claim 1 in which said transverse segments forms an angle of approximately 90° with said longitudinal segment.

4. A distal radial plate for the fixation of a fractured distal radius, said distal radial plate comprising:

(a) a longitudinal segment having a proximal end and a distal end; and (b) a transverse segment having a lateral end and a medial end;

said distal end of said longitudinal segment attached to said transverse segment intermediate said lateral and medial ends of said transverse segment to form a T-shape;

said longitudinal segment having a plurality of spherically recessed holes and having a slot with a proximal end and a distal end; said distal end of said slot having a spherical recess; said proximal end of said slot having a beveled edge which converges distally with the spherical recess of said slot;

said transverse segment having a plurality of spherically recessed holes;

said transverse segments forming an angle of approximately 113° with said longitudinal segment.

* * * * *